United States Patent
Taha et al.

(10) Patent No.: US 10,004,282 B2
(45) Date of Patent: Jun. 26, 2018

(54) SURGICAL GLOVE TAPE

(71) Applicants: Jamal Taha, Cincinnati, OH (US);
Assad Taha, Cincinnati, OH (US)

(72) Inventors: Jamal Taha, Cincinnati, OH (US);
Assad Taha, Cincinnati, OH (US)

( * ) Notice: Subject to any disclaimer, the term of this patent is extended or adjusted under 35 U.S.C. 154(b) by 108 days.

(21) Appl. No.: 15/262,039

(22) Filed: Sep. 12, 2016

(65) Prior Publication Data

US 2016/0376476 A1 Dec. 29, 2016

Related U.S. Application Data (63) Continuation-in-part of application No. 14/585,581, filed on Dec. 30, 2014, now Pat. No. 9,464,213.

(51) Int. Cl.
| | | |
|---|---|---|
| *A41D 13/00* | (2006.01) | |
| *A41D 13/12* | (2006.01) | |
| *A61B 42/10* | (2016.01) | |
| *C09J 7/21* | (2018.01) | |

(52) U.S. Cl.
CPC ..... *A41D 13/0005* (2013.01); *A41D 13/1209* (2013.01); *A61B 42/10* (2016.02); *C09J 7/21* (2018.01); *C09J 2400/263* (2013.01); *C09J 2433/00* (2013.01); *Y10T 428/14* (2015.01)

(58) Field of Classification Search
USPC ....................................... 156/247, 249, 289
See application file for complete search history.

(56) References Cited

U.S. PATENT DOCUMENTS

| | | |
|---|---|---|
| 3,330,275 A | 7/1967 | Jenard et al. |
| 3,381,989 A | 5/1968 | Thomas |
| 4,099,270 A | 7/1978 | Jabour |
| 4,215,684 A | 8/1980 | Westip |
| 4,464,796 A | 8/1984 | Heissenberger et al. |
| 4,665,409 A | 5/1987 | Behrens et al. |
| 4,798,200 A | 1/1989 | Warthen et al. |
| 4,843,651 A | 7/1989 | Gramza et al. |

(Continued)

FOREIGN PATENT DOCUMENTS

| | | |
|---|---|---|
| CA | 2553129 A1 | 11/2005 |
| EP | 2127547 A2 | 12/2009 |
| WO | 9639055 A1 | 12/1996 |

OTHER PUBLICATIONS

Ansell; Gammex® PF, "Powder-Free Latex Surgical Glove: Advanced Powder-Free Latex Gloves for General Surgery", brochure, downloaded on Apr. 10, 2014 at www.ansell.be/medical/pdf/gloves/EN/Gammex%20PF.pdf.

(Continued)

*Primary Examiner* — Sing P Chan
(74) *Attorney, Agent, or Firm* — Thomas E. Lees, LLC (57) ABSTRACT

A surgical glove tape comprises an elongate strip of material, an adhesive, and a release liner. In particular, the elongate strip of material is comprised of a combination of cotton and spandex. The elongate strip of material has a first major surface and a second major surface. Moreover, the elongate strip of material is further characterized by a tab section extending from a first end of the elongate strip of material, and a taping section extending from the tab section. The adhesive coats the second major surface of the elongate strip of material within the taping section of the elongate strip of material. The release liner overlies the adhesive.

20 Claims, 3 Drawing Sheets

(56) References Cited

U.S. PATENT DOCUMENTS

| | | | |
|---|---|---|---|
| 4,845,780 A * | 7/1989 | Reimers | A41D 19/0062 2/160 |
| 4,845,781 A * | 7/1989 | Strickland | A41D 19/0075 2/161.6 |
| 4,884,300 A | 12/1989 | Vistins | |
| 5,020,159 A | 6/1991 | Hellickson | |
| 5,118,381 A * | 6/1992 | Ryder | A61F 15/002 156/289 |
| 5,156,589 A | 10/1992 | Langen et al. | |
| 5,442,816 A | 8/1995 | Seketa | |
| 5,459,879 A * | 10/1995 | Fuchs | A61L 342/10 128/844 |
| 5,483,697 A * | 1/1996 | Fuchs | A61L 342/10 128/844 |
| 5,486,322 A * | 1/1996 | Fuchs | A61L 342/10 264/300 |
| 5,555,561 A | 9/1996 | Plachta et al. | |
| 5,557,806 A | 9/1996 | Caswell et al. | |
| 5,572,743 A * | 11/1996 | Yavitz | A41D 13/1209 2/114 |
| 5,604,933 A | 2/1997 | Stephens | |
| 5,643,668 A * | 7/1997 | Calhoun | B32B 7/04 428/354 |
| 5,693,401 A | 12/1997 | Sommers et al. | |
| 5,734,992 A * | 4/1998 | Ross | A41D 13/08 2/16 |
| 5,867,832 A | 2/1999 | Liu | |
| 6,119,272 A | 9/2000 | Tebbe | |
| 6,301,755 B1 | 10/2001 | Gaber | |
| 8,336,115 B2 | 12/2012 | Jordan et al. | |
| 8,341,768 B2 | 1/2013 | Gellerstedt | |
| 8,677,513 B2 | 3/2014 | Mathis et al. | |
| 9,216,254 B2 * | 12/2015 | Taylor | A61M 5/321 |
| 9,464,213 B2 * | 10/2016 | Taha | C09J 7/041 |
| 2002/0099318 A1 | 7/2002 | Suehr et al. | |
| 2003/0152732 A1 | 8/2003 | Donahue | |
| 2005/0031821 A1 | 2/2005 | Clark | |
| 2005/0031884 A1 * | 2/2005 | Koide | B29C 33/56 428/521 |
| 2005/0223471 A1 * | 10/2005 | Griesbach, III | A41D 13/1209 2/160 |
| 2005/0274453 A1 * | 12/2005 | Anvar | A61B 17/085 156/247 |
| 2006/0185059 A1 | 8/2006 | Taha et al. | |
| 2006/0212991 A1 * | 9/2006 | Noreen | A41D 19/0062 2/161.7 |
| 2007/0000020 A1 * | 1/2007 | Vistins | A41D 19/0062 2/161.1 |
| 2008/0134418 A1 | 6/2008 | Johansson et al. | |
| 2011/0094002 A1 | 4/2011 | Palomo et al. | |
| 2013/0125900 A1 * | 5/2013 | Taylor | A61M 5/321 128/846 |
| 2016/0186016 A1 * | 6/2016 | Taha | C09J 7/04 428/41.8 |
| 2016/0376476 A1 * | 12/2016 | Taha | A41D 13/1209 156/249 |

OTHER PUBLICATIONS

Ultimate Performance; "Ultimate Performance®, UP Kinesiology Taping Guide", brochure, downloaded on Apr. 10, 2014 at http://www.ultimate-performance.co.uk/docs/UP_ktape_guide.pdf.
Derwent Abstract 2001-527913 dated Feb. 15, 2001.

* cited by examiner

SURGICAL GLOVE TAPE

CROSS REFERENCE TO RELATED APPLICATION

This application is a continuation-in-part of U.S. patent application Ser. No. 14/585,581, filed Dec. 30, 2014, now allowed, entitled "SURGICAL GLOVE TAPE", the disclosure of which is hereby incorporated herein by reference.

BACKGROUND

Various aspects of the present invention relate generally to the donning and securement of surgical gloves.

Surgeons are often called upon to perform surgeries where exposure to contamination can create unintended medical complications. For instance, surgeons use aseptic techniques to prevent the contamination of open surgical wounds by isolating the operative site from a surrounding non-sterile environment. In addition to protecting the patient from unintended complications, surgeons and others in an operative site must protect themselves from disease and other harmful effects that result from contact with bodily fluid of the patient undergoing the medical procedure. In this regard, surgeons and others in the operative site often wear sterilized surgical gowns, masks and gloves.

BRIEF SUMMARY

According to aspects of the present disclosure herein, a method of making a surgical glove tape is disclosed. The method comprises providing an elongate strip of material comprised of a combination of cotton and spandex. Here, the elongate strip of material has a first major surface and a second major surface. Further, the elongate strip of material is characterized by a tab section extending from a first end of the elongate strip of material, and a taping section extending from the tab section. The method also comprises coating the second major surface of the elongate strip of material within the tab section (of the elongate strip of material) with a tab section adhesive, and forming a tab strip that covers the tab section adhesive over the tab section. The method still further comprises coating the second major surface of the elongate strip of material within the taping section (of the elongate strip of material) with a taping section adhesive, and providing a release liner that overlies the elongate strip so as to extend past an edge of the tab section of the elongate strip. Given the above, the release liner releasably attaches to the taping section adhesive within the taping section, the release liner overlies, but avoids contact with the tab section adhesive due to the tab strip, and the tab strip prevents contact with the tab section adhesive when the release liner is removed from the elongate strip.

According to further aspects of the present disclosure, a method of securing a surgical glove to a surgical gown is provided. This method utilizes a surgical glove tape having an elongate strip of material comprised of a combination of cotton and spandex, wherein the elongate strip of material has a first major surface and a second major surface. Further, the elongate strip of material is characterized by a tab section extending from a first end of the elongate strip of material, and a taping section extending from the tab section. The surgical glove tape also includes a tab section adhesive that coats the second major surface of the elongate strip of material within the tab section (of the elongate strip of material), and a tab strip that covers the tab section adhesive over the tab section. The surgical glove tape still further includes a taping section adhesive that coats the second major surface of the elongate strip of material within the taping section (of the elongate strip of material), and a release liner that overlies the elongate strip so as to extend past an edge of the tab section of the elongate strip. Moreover, the release liner releasably attaches to the taping section adhesive within the taping section, the release liner overlies, but avoids contact with the tab section adhesive due to the tab strip, and the tab strip prevents contact with the tab section adhesive when the release liner is removed from the elongate strip. With the above structure for the surgical glove tape described, the method comprises donning a surgical gown having sleeves, donning a first surgical glove, and grasping a first strip of the surgical glove tape. The method also comprises holding the tab section of the surgical glove tape in a hand while peeling back a portion of the release liner with the other hand, and applying the surgical glove tape at the intersection between the first glove and the sleeve of the surgical gown. The method yet further comprises wrapping the surgical glove tape around the intersection between the first surgical glove and the sleeve of the surgical gown without stretching the elongate strip of material, and pressing the surgical glove tape against the intersection of the first surgical glove and the sleeve of the surgical gown to form a seal therebetween.

According to still further aspects of the present disclosure, a method of securing a surgical glove to a surgical gown is provided. This method utilizes a surgical glove tape having an elongate strip of material comprised of a combination of cotton and spandex, wherein the elongate strip of material has a first major surface and a second major surface. Further, the elongate strip of material is characterized by a tab section extending from a first end of the elongate strip of material, and a taping section extending from the tab section. The surgical glove tape also includes a tab section adhesive that coats the second major surface of the elongate strip of material within the tab section (of the elongate strip of material), and a tab strip that covers the tab section adhesive over the tab section. The surgical glove tape still further includes a taping section adhesive that coats the second major surface of the elongate strip of material within the taping section (of the elongate strip of material), and a release liner that overlies the elongate strip so as to extend past an edge of the tab section of the elongate strip. Moreover, the release liner releasably attaches to the taping section adhesive within the taping section, the release liner overlies, but avoids contact with the tab section adhesive due to the tab strip, and the tab strip prevents contact with the tab section adhesive when the release liner is removed from the elongate strip. With the above structure for the surgical glove tape described, the method comprises donning a surgical gown having sleeves, donning a surgical glove, and grasping a strip of surgical glove tape. The method also comprises peeling the tab from the tab section of the elongate strip of material, and pressing the tab section against the intersection between the surgical glove and a sleeve of the surgical gown. The method still further comprises peeling back a portion of the release liner with the other hand, and applying the surgical glove tape at the intersection between the surgical glove and the sleeve of the surgical gown. The method still further comprises wrapping the surgical glove tape around the intersection between the surgical glove and the sleeve of the surgical gown without stretching the elongate strip of material, and pressing the surgical glove tape against the intersection of the surgical glove and the sleeve of the surgical gown to form a seal therebetween.

DETAILED DESCRIPTION

Cuffs at wrists of a conventional surgical gown are considered unsterile. If a surgical glove does not cover the cuffs, contamination may occur at an operative site. Here, contamination may occur from the inside-out (i.e., from the surgeon to the environment) or from the outside-in (i.e., from the environment to the surgeon). As such, sterile surgical gloves are typically pulled over the cuff and up the sleeve of the surgical gown. Unfortunately, the conventional surgical glove can roll down the sleeve of the surgeon.

However, according to aspects of the present disclosure herein, a disposable sterile adhesive strip is provided, which is used to retain a surgical glove from rolling down a sleeve of a surgical gown during a surgical procedure.

Figure 1:
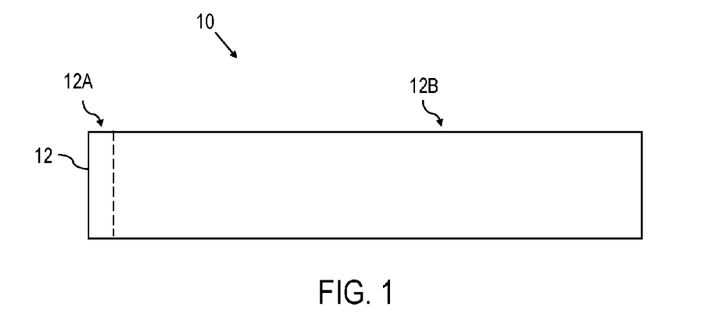
FIG. 1 is a top view of a surgical glove tape, according to aspects of the present disclosure herein.

Referring to drawings and in particular to FIG. 1, a surgical glove tape 10 is illustrated. In general, the surgical glove tape 10 includes an elongate strip of material 12 that defines the tape body. The elongate strip of material 12 includes a first major surface (e.g., a top side as illustrated in FIG. 1) and a second major surface (e.g., a bottom surface, described with reference to FIG. 2). Moreover, the elongate strip of material 12 is further characterized by a tab section 12A extending from a first end of the elongate strip of material 12, and a taping section 12B extending from the tab section 12A. The tab section 12A and the taping section 12B are described in greater detail herein. In alternative embodiments, there may be a tab section 12A on each end of the elongate strip of material 12 thus bookending the taping section 12B, as will be described with reference to the embodiments in FIG. 3 and FIG. 5.

In an example implementation, the elongate strip of material 12 is a sterile cloth comprised of a combination of cotton and spandex (i.e., polyester-polyurethane copolymer), e.g., 95% cotton and 5% spandex. The elongate strip of material 12 may be sterilized, for instance, using Ethylene Oxide. Moreover, the elongate strip of material 12 may have dimensions suitable to tape a surgical glove to a surgical gown. For instance, a working example has a length of 30 centimeters and a width of 6 centimeters. However, other lengths and widths may be utilized. Moreover, the elongate strip of material 12 is preferably resistant to surface wetting. For instance, it may be sufficient for the elongate strip of material 12 to achieve a spray rating of a level 2 (wetting of half of the sprayed surface, e.g., usually through the merging of small discrete wetting areas) to a level 3 (wetting of the sprayed surface only at small discrete areas) when evaluated according to the EN 24920:1992 ISO 4920:1981 standard.

Figure 2:
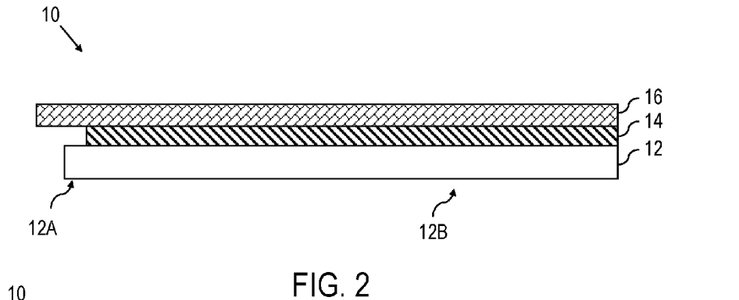
FIG. 2 is a side view of the surgical glove tape of FIG. 1, illustrating the adhesive and release liner layers, according to aspects of the present disclosure herein.

Referring to FIG. 2, a schematic side view of the surgical glove tape 10 is illustrated according to aspects of the present disclosure. As shown, an adhesive 14 coats the second major surface of the elongate strip of material 12 within the taping section 12B of the elongate strip of material 12. However, no adhesive 14 is applied within the tab section 12A of the elongate strip of material 12. For instance, the adhesive 14 may be applied over the entire area of the second major surface of the elongate strip of material 12 within the taping section 12B. In other examples, the adhesive 14 is applied to less than the entirety of the taping section 12B, e.g., by applying the adhesive 14 in a pattern. In a working example, the adhesive is a latex-free, acrylic acid composition. However, other compositions may alternatively be used.

Also as shown, a release liner 16 is positioned so as to overlie the adhesive 14. In more specific examples, the release liner 16 extends past the edge of the adhesive 14 so as to overlie the entirety of the elongate strip of material 12. In further examples, the release liner 16 may extend past one or more of the edges of the elongate strip of material 12. For instance, the release liner 16 may extend past the end edges of the elongate strip of material 12.

In the example implementation of FIG. 2, there is no adhesive 14 over the tab section 12A of the elongate strip of material 12. This facilitates easy peeling of the release liner from the elongate strip of material 12. More particularly, this arrangement makes it easy to wield the surgical glove tape 10 so as to grasp the release liner 16 separately from the elongate strip of material 12 while wearing gloves.

In this regard, the dimensions of the tab section 12A may vary depending upon the properties of the adhesive 14 and the dimensions of the release liner 16 relative to the elongate strip of material 12.

Figure 3:
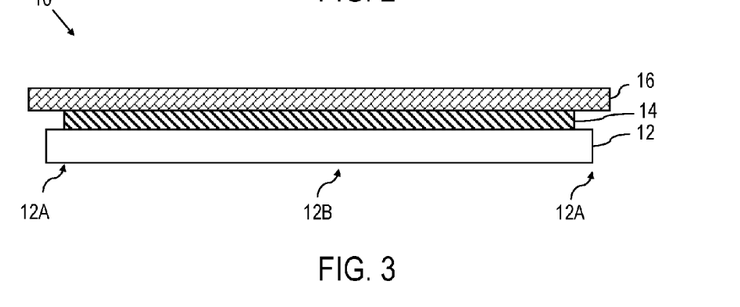
FIG. 3 is a side view of the surgical glove tape of FIG. 1, illustrating the adhesive and release liner layers, according to further aspects of the present disclosure herein.

Referring to FIG. 3, the surgical glove tape 10 is identical to that set out with regard to FIG. 2, except that in this implementation, there is a tab section 12A on both the right end and the left end of the elongate strip of material 12. In this illustrative implementation, adhesive 14 is provided generally in the central portion of the strip, extending out towards, but stopping just shy of the ends of the elongate strip of material 12, leaving a first end region of the elongate strip of material 12 (i.e., a first tab section 12A) and a second end region of the elongate strip of material 12 (i.e., a second tab section 12A), which are free of adhesive 14.

Thus, a tab section 12A (first tab section) extends from a first end of the elongate strip of material and a tab section 12A (second tab section) extends from a second end of the elongate strip of material opposite of the first end so that the taping section lies between the tab sections 12A. Here, the adhesive 14 does not extend to either end of the elongate strip of material 12.

As with the example of FIG. 2, the release liner 16 may be larger in one or more dimensions compared to the elongate strip of material 12. However, this need not be the case, so long as the release liner 16 covers the adhesive 14. The configuration of FIG. 3 allows the surgeon to easily peel either end of the elongate strip of material 12 from the release liner 16, regardless of direction that the surgical glove tape 10 is picked up.

Figure 4:
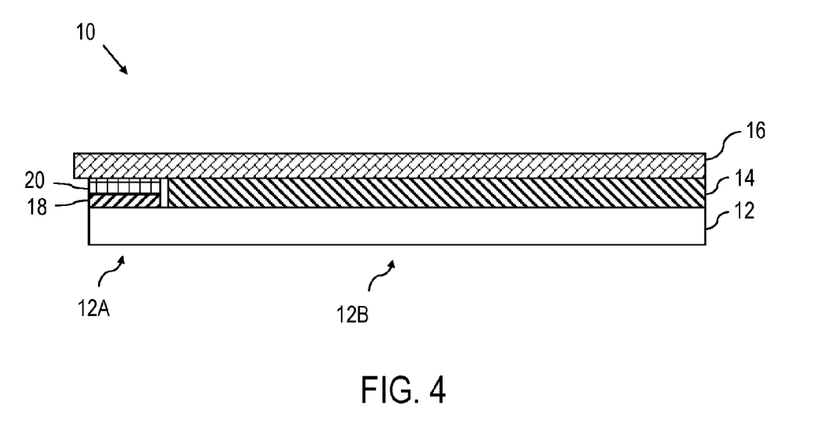
FIG. 4 is a side view of the surgical glove tape of FIG. 1 according to a further aspect of the disclosure, where a tab section of the surgical glove tape includes adhesive and a tab strip.

Referring to FIG. 4, in another working example, the tab section 12A of the elongate strip of material 12 may be covered with an adhesive 18. The adhesive 18 may be the same composition or a different composition of the adhesive 14. Moreover, there may be a small gap between the adhesive within the tab section 12A and the taping section 12B. Alternatively, the adhesive may be continuous, e.g., covering the entirety of the elongate strip of material 12. In this implementation, the designation of adhesive 18 is to indicate that portion of the adhesive over the tab section 12A compared to the adhesive 14 over the taping section 12B.

A tab strip 20 covers the adhesive 18. For instance, the tab strip 20 may overlie the entirety (or a portion) of the tab section 12A. In this regard, the tab strip 20 is not sticky and prevents the adhesive 18 from coming in contact with a person. In this example, the tab strip 20 may be the same material as the material 12. The tab strip 20 may be the same material as the release liner 16, e.g., a film liner. For instance, the tab strip 20 may be separate from the release liner 16, or is otherwise easily separable from the release liner 16, e.g., via perforations, slits, tear lines, etc. Alternatively, the tab strip 20 may be a different material, e.g., a non-release material. In this implementation, the release liner 16 may extend over the tab strip 20. Also, as with the embodiment of FIGS. 2 and 3, the release liner 16 may extend beyond one or more of the edges of the elongate strip of material 12.

In illustrative implementations, the tab strip 20 is not intended to separate from the adhesive 18. Rather, the tab is intended to provide an easy way for the surgeon to wield the surgical glove tape 10 while wearing surgical gloves by making it easy to separate the release liner 16 from the elongate strip of material 12 about an end thereof, e.g., without coming in contact with the adhesive 14.

Figure 5:
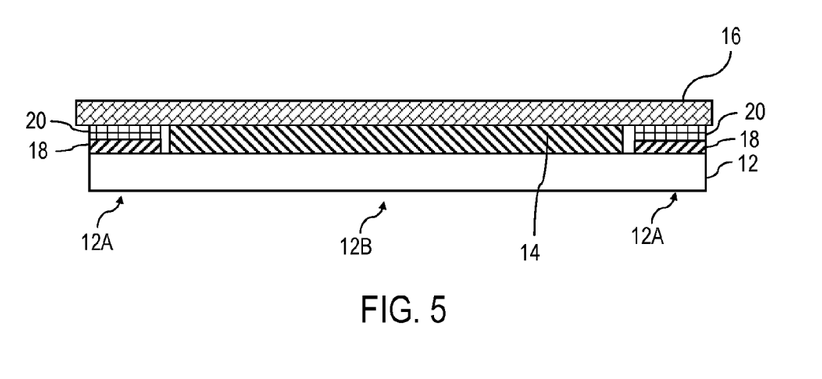
FIG. 5 is a side view of the surgical glove tape of FIG. 1 according to a further aspect of the disclosure, where a tab section of the surgical glove tape includes adhesive and a tab strip, and is provided on each end of the surgical glove tape.

Referring to FIG. 5, the illustrated embodiment is identical to that illustrated with regard to FIG. 4, except that there is a tab section 12A, and corresponding adhesive 18 and tab strip 20 on each end of the elongate strip of material 12. Analogous to the embodiment of FIG. 3, this configuration allows the surgeon to easily peel either end of the elongate strip of material 12 from the release liner 16, regardless of direction that the surgical glove tape 10 is picked up.

Thus, for instance, a tab section 12A (first tab section) extends from a first end of the elongate strip of material 12 and tab section 12A (second tab section) extends from a second end of the elongate strip of material 12 opposite of the first end so that the taping section 12B lies between the tab sections 12A. A coating of adhesive 18 covers each tab section 12A on the second major surface of the elongate strip of material 12. Moreover, a first tab strip 20 covers the adhesive 18 over a first one of the tab sections 12A and a second tab strip 20 covers the adhesive 18 over a second one of the tab sections 12A. Here, each tab strip 20 may be derived from the release liner material, e.g., so as to be separable from the release liner 16 over the taping section 12B (e.g., where the tab strip is release liner material). Alternatively, each tab strip 20 may be distinct and separate from the release liner 16 over the taping section 12B. In this implementation, the release liner 16 may overlie the tab strips 20.

Figure 6:
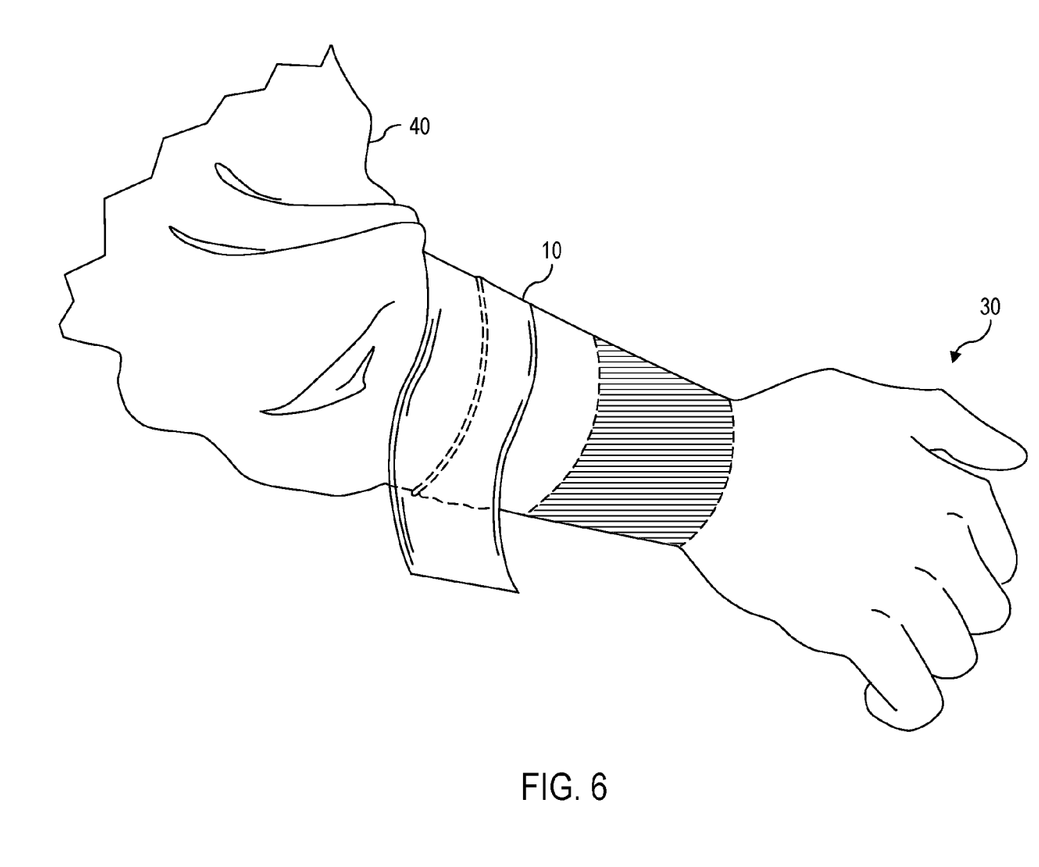
FIG. 6 is a view illustrating a surgeon donning a glove using the surgical glove tape of FIG. 1.

Referring to FIG. 6, an illustration shows the surgical glove tape 10 being used to secure a surgical glove 30 over a sleeve of a surgical gown 40. When a surgeon is preparing for surgery, the surgeon may don surgical gloves 30 and a gown 40. To secure the gloves 30 to the sleeves of the gown 40, the surgeon places a finger between the release liner 16 and the elongate strip of material 12 at the tab section 12A. For instance, the surgeon may grasp the surface of the release liner 16 between a finger and a thumb of a first hand. With the other hand, the surgeon can grasp the elongate strip of material 12 within the tab section 12A and peel the release liner 16 back exposing adhesive 14. Because there is no adhesive in the tab section (FIG. 2 or FIG. 3) or the adhesive is covered by a tab (FIG. 4 or FIG. 5), the surgical glove tape 10 does not stick to the surgeon's gloves or fingers. The surgeon then peels back a portion of the release liner exposing a portion of the adhesive 14. The surgical glove tape 10 may then be applied between the surgical glove 30 and sleeve of the surgical gown 40. The surgical glove tape 10 is then wrapped around the surgical glove 30 as the release liner 16 is peeled from the elongate strip of material 12.

Once a portion of the adhesive 14 is exposed, the surgeon presses the exposed portion over the interface between the surgical glove 30 and the sleeve of the surgical gown 40. Then, the surgeon can remove the remainder of the release liner 16 from the elongate strip of material 12 while simultaneously wrapping the surgical glove tape 10 around the interface between the glove 30 and the gown 40. After the elongate strip of material 12 has been wrapped entirely around the interface, the surgeon may apply pressure to ensure the surgical glove tape 10 is properly adhered to the glove 30 and gown 40.

In use, constant compression of the surgical glove tape 10 is not required. Moreover, stretching and pulling of the surgical glove tape 10 is not required to properly secure a surgical glove 30 to a sleeve of a surgical gown 40. In this regard, pulling and stretching is not recommended. This allows the surgeon to move more freely because the surgical glove tape 10 is not pulled tightly against the arm of the surgeon.

With reference to FIGS. 1-3 and 6, a method of securing a surgical glove to a surgical gown, comprises donning a surgical gown having sleeves, and donning a surgical glove. The method also comprises grasping a strip of surgical glove tape. The surgical glove tape is analogous to that set out with regard to FIGS. 1-3, and 6. In particular, the surgical glove tape has an elongate strip of material comprised of a combination of cotton and spandex, wherein the elongate strip of material has a first major surface and a second major surface. The elongate strip of material is further characterized by a tab section extending from a first end of the elongate strip of material, and a taping section extending from the tab section. An adhesive coats the second major surface of the elongate strip of material within the taping section of the elongate strip of material, and a release liner overlies the adhesive.

The method further comprises holding the tab section of the surgical glove tape in a hand while peeling back a portion of the release liner with the other hand and applying the surgical glove tape at the intersection between the glove and the sleeve of the surgical gown. The method still further comprises wrapping the surgical glove tape around the intersection between the surgical glove and the sleeve of the surgical gown without stretching the elongate strip of material and pressing the surgical glove tape against the intersection of the surgical glove and the sleeve of the surgical gown to form a seal therebetween.

With reference to FIGS. 1, 4-5 and 6, a method of securing a surgical glove to a surgical gown comprises donning a surgical gown having sleeves and donning a surgical glove. The method also comprises grasping a strip of surgical glove tape. Here, with particular reference to FIG. 4 and FIG. 5, the surgical glove tape has an elongate strip of material comprised of a combination of cotton and spandex, wherein the elongate strip of material has a first major surface and a second major surface. The elongate strip of material is further characterized by a tab section extending from a first end of the elongate strip of material, and a taping section extending from the tab section. Also, an adhesive coats the second major surface of the elongate strip of material within the taping section of the elongate strip of material, and a release liner overlies the adhesive. Still further, a coating of adhesive covers the tab section on the second major surface of the elongate strip of material, and a tab strip covers the adhesive over the tab section, where the tab strip is separate or otherwise separable from the release liner over the taping section.

The method still further comprises peeling the tab from the tab section of the elongate strip of material, and pressing the tab section against the intersection between the surgical glove and a sleeve of the surgical gown. The method also comprises peeling back a portion of the release liner with the other hand, and applying the surgical glove tape at the intersection between the surgical glove and the sleeve of the surgical gown. The method then comprises wrapping the surgical glove tape around the intersection between the surgical glove and the sleeve of the surgical gown without stretching the elongate strip of material, and pressing the surgical glove tape against the intersection of the surgical glove and the sleeve of the surgical gown to form a seal therebetween.

With reference to the FIGURES generally, the adhesive 14, adhesive 18 and combinations thereof, as used herein is not subject to attack by water and bodily fluids that the surgeon commonly encounters when performing surgical procedures. In this regard, the surgical glove tape 10 herein provides a seal between the sleeve of a surgical gown and a surgical glove that is not broken during an operating procedure. Also, the surgical glove tape 10 can be applied by the surgeon directly without requiring the assistance of another person. Once the procedure is complete, the surgical glove tape 10 is unwrapped and disposed of with other waste.

The surgical tape herein eliminates a common problem that can affect the health of the surgeon. When a surgical glove is pulled over the cuff and sleeve of a surgical gown, channeling can occur that can allow bodily fluid from the patient to run under the surgical glove and down to the wrist area of the surgeon. Thus, the channeling effect can potentially allow bodily fluid from the patient to contact the surgeon's skin. However, the surgical tape herein forms a seal around the intersection between the surgical glove and the sleeve of the surgical gown that is impervious to fluids, even during extended operations lasting numerous hours.

Moreover, because the surgical glove tape is not stretched, there is no pulling or tugging that would otherwise interfere with the motions of the surgeon, providing not only more comfort, but a more consistent operating environment. However, because of the adhesive, a seal is formed by loose wrapping of the surgical glove tape, and the pressing of the tape against the boundary of the surgical glove and the sleeve of the surgical gown. Once a first glove is properly taped, the process is repeated for the other surgical glove.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. Aspects of the invention were chosen and described in order to best explain the principles of the invention and the practical application, and to enable others of ordinary skill in the art to understand the invention for various embodiments with various modifications as are suited to the particular use contemplated.

What is claimed is:

1. A method of making a surgical glove tape, comprising:
   providing an elongate strip of material comprised of a combination of cotton and spandex, wherein:
      the elongate strip of material has a first major surface and a second major surface; and
      the elongate strip of material is characterized by a tab section extending from a first end of the elongate strip of material, and a taping section extending from the tab section;
   coating the second major surface of the elongate strip of material within the tab section of the elongate strip of material with a tab section adhesive;
   forming a tab strip that covers the tab section adhesive over the tab section;
   coating the second major surface of the elongate strip of material within the taping section of the elongate strip of material with a taping section adhesive; and
   providing a release liner that overlies the elongate strip so as to extend past an edge of the tab section of the elongate strip;
   wherein:
      the release liner releasably attaches to the taping section adhesive within the taping section;
      the release liner overlies, but avoids contact with the tab section adhesive due to the tab strip; and
      the tab strip prevents contact with the tab section adhesive when the release liner is removed from the elongate strip.

2. The method of claim 1, wherein:
   providing an elongate strip of material comprises providing the elongate strip of material comprised of 95% cotton and 5% spandex.

3. The method of claim 1, wherein:
   providing an elongate strip of material comprises providing the elongate strip of material being at least 30 centimeters in length and at least 6 centimeters in width.

4. The method of claim 1 further comprising:
   providing the taping section adhesive as a latex-free, acrylic acid composition.

5. The method of claim 1, wherein providing an elongate strip of material comprises providing the elongate strip such that the tab section comprises a first tab section, the tab section adhesive comprises a first tab section adhesive, and the tab strip comprises a first tab strip;
further comprising:
providing a second tab section extending from a second end of the elongate strip of material opposite of the first end so that the taping section lies between the first tab section and the second tab section;
coating with a second tab adhesive, the second major surface of the elongate strip of material within the second tab section of the elongate strip of material; and
covering the second tab adhesive over the second tab section with a second tab strip, the second tab strip configured such that the release liner is spaced from the second tab section adhesive by the second tab strip, and the second tab strip prevents contact with the second tab section adhesive.

6. The method of claim 1 further comprising:
extending the release liner past the end edges of the elongate strip of material.

7. The method of claim 1 further comprising:
using the same adhesive for the tab section adhesive and the taping section adhesive; and
providing the tab strip that covers the tab section adhesive over the tab section to be separable from the release liner over the taping section.

8. The method of claim 1, wherein providing an elongate strip of material comprises providing the elongate strip such that the tab section comprises a first tab section, the tab section adhesive comprises a first tab section adhesive, and the tab strip comprises a first tab strip;
further comprising:
providing a second tab section extending from a second end of the elongate strip of material opposite of the first end so that the taping section lies between the first tab section and the second tab section;
providing a second tab section adhesive that covers the second tab section, wherein the first tab second adhesive and the second tab section adhesive are the same adhesive composition; and
providing a second tab strip that covers the second tab section adhesive over the second tab section;
wherein:
each of the first tab strip and the second tab strip is separable from the release liner over the taping section.

9. The method of claim 1 further comprising:
providing the first tab strip that covers the first tab section adhesive as a strip that is distinct and separate from the release liner over the taping section.

10. The method of claim 1, wherein:
providing the elongate strip of material comprises providing a strip that does not exceed 30 centimeters in length and 6 centimeters in width.

11. The method of claim 1, wherein:
providing the elongate strip of material comprises providing an elongate strip of material that is sterilized with Ethylene Oxide.

12. The method of claim 1 further comprising:
applying the first coating of adhesive and the second coating of adhesive to the elongate strip of material so as to leave a gap between adhesive in the taping section and adhesive in the tab section.

13. The method of claim 1 further comprising:
overlying the release liner over the elongate strip so as to extend past an edge of the tab section of the elongate strip.

14. The method of claim 1, wherein providing an elongate strip of material comprises providing the tab section as a first tab section, providing the tab section adhesive as a first tab section adhesive, and providing the tab strip as a first tab strip;
the method further comprising:
providing a second tab section extending from a second end of the elongate strip of material opposite of the first end so that the taping section lies between the first tab section and the second tab section;
providing a second tab section adhesive that covers the second tab section on the second major surface of the elongate strip of material, where the first tab section adhesive, the taping section adhesive, and the second tab section adhesive are the same adhesive composition; and
providing a second tab strip that covers the second tab section adhesive over the second tab section;
wherein:
each of the first tab strip and the second tab strip are distinct and separate from the release liner over the taping section;
the first tab section adhesive, the taping section adhesive, and the second tab section adhesive are applied such that a first gap of no adhesive exists on the elongate strip of material between the first tab section and the taping section, and a second gap of no adhesive exists on the elongate strip of material between the taping section and the second tab section; and
the release liner overlies the elongate strip so as to extend past an edge of the first tab section of the elongate strip of material and past an edge of the second tab section of the elongate strip of material.

15. A method of securing a surgical glove to a surgical gown, comprising:
donning a surgical gown having sleeves;
donning a first surgical glove;
grasping a first strip of surgical glove tape, the surgical glove tape having:
an elongate strip of material comprised of a combination of cotton and spandex, wherein:
the elongate strip of material has a first major surface and a second major surface; and
the elongate strip of material is characterized by a tab section extending from a first end of the elongate strip of material, and a taping section extending from the tab section;
a tab section adhesive that coats the second major surface of the elongate strip of material within the tab section of the elongate strip of material;
a tab strip that covers the tab section adhesive over the tab section;
a taping section adhesive that coats the second major surface of the elongate strip of material within the taping section of the elongate strip of material; and
a release liner that overlies the elongate strip so as to extend past an edge of the tab section of the elongate strip;
wherein:
the release liner releasably attaches to the taping section adhesive within the taping section;
the release liner overlies, but avoids contact with the tab section adhesive due to the tab strip; and the tab strip prevents contact with the tab section adhesive when the release liner is removed from the elongate strip;

holding the tab section of the surgical glove tape in a hand while peeling back a portion of the release liner with the other hand;

applying the surgical glove tape at the intersection between the first glove and the sleeve of the surgical gown;

wrapping the surgical glove tape around the intersection between the first surgical glove and the sleeve of the surgical gown without stretching the elongate strip of material; and pressing the surgical glove tape against the intersection of the first surgical glove and the sleeve of the surgical gown to form a seal therebetween.

16. The method of claim 15, wherein:
wrapping the surgical glove tape around the intersection between the first surgical glove and the sleeve of the surgical gown comprises wrapping the surgical tape around the first surgical glove as the release liner is peeled from the elongate strip of material.

17. The method of claim 15 further comprising:
donning a second surgical glove on a hand opposite the hand wearing the first surgical glove;
grasping a second piece of the surgical glove tape;
holding the tab section of the second piece of surgical glove tape in a hand while peeling back a portion of the release liner with the other hand;
applying the second piece of the surgical glove tape at the intersection between the second surgical glove and a corresponding sleeve of the surgical gown;
wrapping the second piece of the surgical glove tape around the intersection between the second surgical glove and the corresponding sleeve of the surgical gown without stretching the elongate strip of material; and
pressing the second piece of the surgical glove tape against the intersection of the second surgical glove and the corresponding sleeve of the surgical gown to form a seal therebetween.

18. A method of securing a surgical glove to a surgical gown, comprising:
donning a surgical gown having sleeves;
donning a surgical glove;
grasping a strip of surgical glove tape, the surgical glove tape having:
an elongate strip of material comprised of a combination of cotton and spandex, wherein:
the elongate strip of material has a first major surface and a second major surface; and
the elongate strip of material is characterized by a tab section extending from a first end of the elongate strip of material, and a taping section extending from the tab section;
a tab section adhesive that coats the second major surface of the elongate strip of material within the tab section of the elongate strip of material;
a tab strip that covers the tab section adhesive over the tab section;
a taping section adhesive that coats the second major surface of the elongate strip of material within the taping section of the elongate strip of material; and
a release liner that overlies the elongate strip so as to extend past an edge of the tab section of the elongate strip;
wherein:
the release liner releasably attaches to the taping section adhesive within the taping section;
the release liner overlies, but avoids contact with the tab section adhesive due to the tab strip; and
the tab strip prevents contact with the tab section adhesive when the release liner is removed from the elongate strip;
peeling the tab from the tab section of the elongate strip of material;
pressing the tab section against the intersection between the surgical glove and a sleeve of the surgical gown;
peeling back a portion of the release liner with the other hand;
applying the surgical glove tape at the intersection between the surgical glove and the sleeve of the surgical gown;
wrapping the surgical glove tape around the intersection between the surgical glove and the sleeve of the surgical gown without stretching the elongate strip of material; and
pressing the surgical glove tape against the intersection of the surgical glove and the sleeve of the surgical gown to form a seal therebetween.

19. The method of claim 18, wherein:
wrapping the surgical glove tape around the intersection between the surgical glove and the sleeve of the surgical gown comprises wrapping the surgical tape around the first surgical glove as the release liner is peeled from the elongate strip of material.

20. The method of claim 18 further comprising pressing the surgical glove tape against the intersection of the surgical glove and the sleeve of the surgical gown so as to avoid channeling of fluid that would otherwise allow bodily fluid from the patient to run under the surgical glove and down to the wrist area of the surgeon.

* * * * *